(12) United States Patent
Stout et al.

(10) Patent No.: US 7,094,558 B2
(45) Date of Patent: Aug. 22, 2006

(54) METHODS OF DETERMINING ACTIVE LEVELS OF DRUGS IN FLUID SAMPLES

(75) Inventors: Robert L. Stout, Overland Park, KS (US); Sue Min Chien, Lenexa, KS (US); Steve H. Dunham, Kansas City, MO (US)

(73) Assignee: Clinical Reference Laboratory, Lenexa, KS (US)

( * ) Notice: Subject to any disclaimer, the term of this patent is extended or adjusted under 35 U.S.C. 154(b) by 0 days.

(21) Appl. No.: 10/037,772

(22) Filed: Nov. 9, 2001

(65) Prior Publication Data

US 2003/0100029 A1    May 29, 2003

(51) Int. Cl.
G01N 33/53    (2006.01)
G01N 3/542    (2006.01)

(52) U.S. Cl. ...................................... 435/7.9
(58) Field of Classification Search ................ 435/7.2, 435/7.93, 7.94, 7.95, 7.9; 530/316, 800, 530/829, 834, 836, 851, 864
See application file for complete search history.

(56) References Cited

U.S. PATENT DOCUMENTS

| | | | |
|---|---|---|---|
| 3,899,397 A | 8/1975 | Morin et al. | |
| 4,242,446 A | 12/1980 | Madappally | |
| 4,276,378 A | 6/1981 | Ryan et al. | |
| 4,335,041 A * | 6/1982 | Ryan et al. | 530/331 |
| 4,792,614 A | 12/1988 | Fobare et al. | |
| 5,216,015 A | 6/1993 | McGarry et al. | |
| 5,369,015 A | 11/1994 | Yoshikawa et al. | |
| 5,378,603 A | 1/1995 | Brown et al. | |
| 5,385,929 A | 1/1995 | Bjorge et al. | |
| 5,407,803 A * | 4/1995 | Brunner et al. | 435/7.4 |
| 5,498,524 A * | 3/1996 | Hall | 435/7.1 |
| 5,527,688 A | 6/1996 | Mallia | |
| 5,576,177 A | 11/1996 | Fridland et al. | |

OTHER PUBLICATIONS

Weinshilboum et al. American Journal of Human Genetics, 1980, vol. 32, pp. 651-662.*
Alegret et al. European Journal of Pharmacology, 1998, vol. 347, pp. 283-291.*

* cited by examiner

*Primary Examiner*—Ralph Gitomer
*Assistant Examiner*—Kailash C. Srivastava
(74) *Attorney, Agent, or Firm*—Hovey Williams LLP

(57) ABSTRACT

Methods for determining the presence and level of active drugs in fluid samples are provided. Advantageously, entire families or classes of drugs can be tested for in one test by identifying the enzyme or receptor upon which members of that drug family act and measuring enzyme activity levels or binding activity levels of receptors. Methods for establishing standard activity levels of these drugs based upon results from samples having known quantities of drug therein are also provided.

10 Claims, No Drawings

METHODS OF DETERMINING ACTIVE LEVELS OF DRUGS IN FLUID SAMPLES

BACKGROUND OF THE INVENTION

1. Field of the Invention

The present invention is concerned with the screening for the presence of drugs in fluid samples. More particularly, the present invention is concerned with screening for the presence of drugs in fluid samples which may or may not contain any drugs being screened for. Still more particularly, the present invention is concerned with the screening for the presence of drugs in fluid samples when it is known that the individual providing the fluid sample is on drugs and the screening procedure can help determine proper medication levels. In the instance where it is not known whether or not the individual providing the sample is on any drugs, the present invention is particularly useful in that it identifies the presence of drug families rather than discreet drugs. The same is true for when it is known that the individual providing the sample is supposed to be on a drug that is in a particular family of drugs whereby the screening procedures can be used to determine compliance with taking prescribed medications. Even more particularly, the present invention utilizes a screening technique which identifies the presence of at least one member of a family of drugs by the effects of the drugs on specific enzymes or receptors which are acted upon by the specific families of drugs.

2. Description of the Prior Art

The laboratory screening of drugs, both prescription and non-prescription, is typically by a form of immunodetection which relies on the development of a specific antibody to the drug or compound being screened for. This antibody is then used to detect the drug in a sample which may or may not contain the drug or compound of interest. A major hurdle which needs to be overcome to accomplish immunodetection using this method is the development of an antibody that is specific for each drug. The antibody must be produced with a sufficient titer, a measure of concentration, to efficiently detect the presence of the drug. Additionally, the antibody must have sufficient specificity to react only with the drug of interest so that accurate results may be obtained. While these requirements are normally obtainable, they inherently result in a system with severe limitations. The greatest of these limitations is the detection of the drug after it is no longer biologically active.

Drugs may be broadly classified into one of two categories. The first type of drug is active in the form that is present in the drug as taken by an individual. This category of drugs requires no structural modification and the drugs in this class are therapeutically active in the medication. The second category of drugs requires a structural change before becoming therapeutically active. In both categories, additional metabolites may also be as active as the parent compound or its first metabolite while other metabolites may have little or no activity. This drastically increases the difficulty in determining the amount of therapeutically active drug present in any fluid sample taken from an individual. Due to the similarity of metabolite structures with the drug as taken or with other metabolites, the metabolites may also contribute to the immunodetection signal so that, regardless of prodrug or metabolite, the signal would be related to total drug exposure. In some instances a metabolite may be therapeutically inactive while still being detected by the antibody developed to detect the drug. In this scenario, immunological detection would overestimate the concentration of active drug present. The opposite problem may occur where a detected metabolite has an even greater activity than the parent drug. In this scenario, immunological detection would underestimate the concentration of active drug present. Thus, current immunodetection methods cannot differentiate the biological activity of the drug or its metabolites. The result is a system which is good at detection of the presence of a drug but totally ineffective at the more important determination of the amount of active drug present. Moreover, metabolites which are similar in structure, regardless of their activity level, may also be identified and thereby further contribute to an inaccurate determination of the concentration of active drug present in the sample tested. Accordingly, one thing needed in the art is a drug screening test which only determines or detects the presence or levels of active drugs in fluid samples.

Many drugs and classes of drugs produce their effect by activational inhibition of specific receptors or activation or inhibition of specific enzymes. Often, an entire class of drugs will produce the same effect on a specific receptor or enzyme, thereby resulting in the therapeutic effect. In the case of drugs and classes of drugs effecting receptors, a drug may bind to a receptor site, thereby inhibiting the binding of the natural activators or inhibitors. Alternatively, the drug may react in the receptor site and irreversibly modify the structure or shape of the receptor, thereby resulting in its inactivation. Other methods of inhibition include binding to other regulatory sites present on the receptor, interfering with cofactor binding, or interaction with other cell surface molecules required for receptor action. Irrespective of the method of inactivation or inhibition, the receptor no longer works with its normal efficiency. Accordingly, another thing needed in the art is a drug screening test which identifies drug presence by determining effects on specific receptors. The usefulness of such a test could be greatly increased if the test could identify the presence of a class of drugs regardless of which specific drug in that class was actually present.

In the case of drugs which effect the activation or inhibition of specific enzymes, a drug may bind to an enzyme's catalytic site and inhibit the binding of the natural substrate. Alternatively, the drug may react in the catalytic site and irreversibly modify the enzyme, thereby resulting in its inactivation. Other methods of inhibition include binding to the regulatory sites present on the enzyme, interfering with cofactor binding, or interaction with the normal substrate, thereby limiting its binding to the enzyme. Irrespective of the method of inactivation or inhibition, the enzyme no longer works with its normal efficiency. In reality, the drug and/or its metabolites have reduced the enzyme's catalytic rate. Therefore, another thing needed in the art is a drug screening test which identifies drug presence by determining enzyme activity. Again, the usefulness of such a test could be greatly increased if the test could identify the presence of an entire class of drugs, regardless of which specific drug in that class was actually present.

SUMMARY OF THE INVENTION

The present invention provides a novel approach for determining the presence of drugs in fluid samples. Advantageously, entire families of drugs are identified using the present invention so that one test can provide information on what type of drug is present in a fluid sample. The methods are based on the effects an active drug has on either a target enzyme or a receptor. In the case of drugs which exert their effects on enzymes, the enzymes may be activated or inhibited by the drug binding to the enzyme's catalytic site, thereby inhibiting the binding of the natural substrate. Captopril is a good example of a drug that exhibits this type of competitive inhibition. Captopril is a member of the drug family or class known as Angiotensin Converting Enzyme (ACE) inhibitors which includes the drugs benazepril, captopril, enalapril, fosinopril, lisinopril, quinapril, moexipril, ramipril, and trandolapril. This class or family of drugs assists in regulating blood pressure by inhibiting the conversion of angiotensin I to angiotensin II which is a powerful vasoconstrictor that helps regulate blood pressure, renal blood flow, and blood volume. If there is an excess amount of angiotensin II, which can be caused by the enzymatic action of ACE, blood pressure increases. ACE inhibiting drugs prevent the cleavage of angiotensin I to angiotensin II, thereby reducing blood pressure.

As noted above, the laboratory screening of drugs is typically by a form of immunodetection. In the case of the ACE inhibiting class of drugs, different antibodies must be developed for nearly every drug as the members of this drug class have dissimilar structures. Additionally, most ACE inhibiting drugs have metabolites that also demonstrate varying degrees of activity and, due to structural similarities, many of these metabolites will be detected, regardless of their activity level, using an antibody-based approach. Thus, when screening for use of this type of drug, one must first know which specific ACE inhibitor is being used and any results may include a number of false positives which occur when metabolites which are inactive or have low activity are identified by the antibody, and thereby contribute to a determination that the sample tested is positive for the drug. Such a test does not really provide the needed information of how much active drug is present in a patient's system. If the specific drug is not known, a number of different tests may have to be run until the specific drug is identified.

However, because all members of the ACE-inhibiting drug family act on the same enzyme, the present invention can be used for the detection of the entire family. Advantageously, the active metabolites will also be identified, thereby providing results of the amount of active drug present in a patient's system. Thus, the invention may be used to screen samples for the presence of a class of drugs including their active metabolites. It may also be used to monitor patient compliance or to determine why one drug appears to be more effective in a particular patient. Finally, the present invention will be useful in emergency type situations where it is necessary to quickly ascertain what types of drugs a patient is on, thereby potentially avoiding dangerous drug interactions or needless dosing of additional medications.

The present invention is also useful in screening for the presence of drugs or families of drugs which exert their effects by reacting in an enzyme's catalytic site, irreversibly modifying and inactivating the enzyme, binding to other regulatory sites present on the enzyme, interfering with cofactor binding, or interaction with the normal substrate and limiting its binding to the enzyme.

To test for the presence of a drug or class of drugs, a sample of fluid is obtained from a patient. The substrate upon which the enzyme acts is then added to the sample and the activity of the enzyme is determined. If the activity of the enzyme is reduced in comparison to a control sample having no drug present, the sample is deemed positive for that class of drugs. Preferably, a set of standards will be set up using methods of the present invention. These standards would be established by testing samples that have a known quantity of active drug present. Results from such controlled testing could then be used comparatively to determine drug presence and levels in samples having unknown amounts of drug present.

Other classes of drugs exert their effects on specific receptors and therefore can also be identified by using methods of the present invention. The family of drugs commonly called the "beta-blockers," which includes the drugs atenolol, propranolol, metoprolol, nadolol, pindolol, timolol, cavediol, and sotalol, are an example of this class of drug. Members of this class or family of drugs act as competitive antagonists at the adrenergic beta receptors and reduce the symptoms connected with hypertension, cardiac arrhythmias, migraine headaches, and other disorders related to the sympathetic nervous system. Adrenergic receptors form the interface between the nerves that serve the heart, blood vessels and kidneys and the organs themselves. Catecholamines such as norepinephrine and dopamine are released from sympathetic nerve terminals and bind to adrenergic receptors on the surface of target cells, thereby activating receptors, which modify the functions of these cells. Beta-blocking drugs reduce receptor occupancy by catecholamines and other beta agonists by competitively binding to these receptors. Adrenaline (also known as epinephrine) is classified as a catecholamine hormone and it is mainly the effects of adrenaline on the body's beta-receptors that are blocked by beta-blockers.

Again, because one test can identify the presence of an active member of a drug class in a sample, time will not have to be spent developing a specific antibody for each member of a drug family. Additionally, information regarding patient compliance with taking medication or efficient detection of active medication in a patient's system are also possible using the present invention.

To identify the presence or level of drugs acting on specific receptors, a sample of fluid is obtained from a patient. Radiolabeled ligand, which binds to the receptor of interest, is added to the sample and the mixture is put into a test tube containing the receptor. If the sample contains a drug, which binds to the receptor, the drug will compete with the radiolabeled ligand for the receptor sites during an incubation period. After incubation, the tubes are centrifuged and decanted, leaving the membranes with bound drug and radiolabeled ligand in the tubes. Gamma counter measures the radioactive tracer activity bound to the receptors in the tube. The amount of activity is inversely proportional to the amount of unlabeled drug in the sample. Of course, standards can also be established using methods described above so that the presence of drugs as well as levels of those drugs can be determined from any sample.

It is understood that when the term "active drug" is used herein, the term encompasses drugs, which are therapeutically active as taken as well as drugs, which have changed in structure before becoming therapeutically active. The term also encompasses metabolites that are therapeutically active. Additionally, the terms "family" and "class" are used interchangeably when referring to drugs having similar therapeutic properties.

DETAILED DESCRIPTION OF THE PREFERRED EMBODIMENT

The following examples set forth preferred embodiments of the present invention. It is to be understood, however, that these examples are provided by way of illustration and nothing therein should be taken as a limitation upon the overall scope of the invention.

EXAMPLE 1

This example tested for the presence of an ACE-inhibiting drug in a fluid sample taken from an individual by measuring enzyme inhibition in the fluid sample.

Materials and Methods

The synthetic pentapeptide substrate, n-(3(2-furyl)acryloyl)-L-phenylanaylglycylglycine(FAPGG) (Sigma Chemical Company, St Louis, Mo., Cat # 305-10) was reconstituted in a bottle with 5 ml of deionized water and left standing for five minutes. The bottle was then inverted a few times and then put on a shaker (Clay Adams CA6000 Centrifuge Becton Dickinson Microbiology System Sparks, Md.) at speed setting 2 for ten minutes. The ACE serum used for this Example was derived from a serum pool consisting of human serum samples which had been tested for ACE activity. However, it is also commercially available through Sigma as part of a kit. All samples, which had an ACE activity greater than 50 units per liter, were combined to form the ACE serum pool. This serum pool was diluted 1:4 with Tris buffer (pH 8.2, 0.136 M) and used as the enzyme source. The Tris buffer (Tris (hydroxymethyl) aminomethane, Sigma Chemical Company, Cat # 25-285-9, Lot # 27H5726 m.w.121.1) was prepared by dissolving 1.695 g Tris base in 50 ml deionized water in a 100 milliliter graduated cylinder. The pH was adjusted to 8.2 with 6 N hydrochloric acid. The stock solution for the inhibitor was 50 mM Captopril (Sigma Chemical Company, Cat #4020, Lot #37H120) that was made by dissolving 10.86 mg Captopril in 1 ml 0.136 mM Tris Buffer. A positive assay control was prepared by diluting the 50 mM Captopril stock. Ten (10) microliters of 50 mM Captopril stock was diluted with 1 milliliter of 0.136M Tris-HCL buffer, pH 8.2. The positive assay control has a normal concentration of 0.5 mM Captopril. A cut-off level of control was prepared by dilution of the 0.5 mM Captopril positive control with Tris buffer. 200 microliters of 0.5 mM Captopril was diluted with 1.8 milliliters of 0.136 M Tris buffer, pH 8.2. Finally, a negative control of Captopril was prepared by a 1:10 dilution of the cutoff control. 200 μl of the 0.5 mM Captopril cutoff control was diluted with 1.8 ml of the Tris Buffer.

Using the above-described reagents, a Hamilton MicroLab AT pipetting station was used to transfer 100 μl of the ACE serum in Tris buffer to each well of a microtiter plate. Next, 25 μl of the cut-off level calibrator, controls and unknowns were added to their corresponding well locations with the Hamilton MicroLab AT, as shown in Table 1.

TABLE 1

| Wells | A1 | B1 | C1 | D1 | E1 | F1 | G1 | H1 |
|---|---|---|---|---|---|---|---|---|
| | Serum Control | | Negative Control | | Cutoff Calibrator | | Positive Control | |

Five different patient samples were then added to five other wells. The microtiter plate was shaker on Titer Plate Shaker (Lab Line Instruments, Inc. Melrose, Ill.) at a setting of 2 for at least five minutes before pipetting 100 μl of the substrate FAPGG into each well. Next, solution was mixed by shaking the microtiter plate on the shaker at a speed setting of 2 for one minute. The microtiter plate was placed in the Spectra Mac Plus (Molecular Devices, Sunnyvale, Calif.) plate reader and the optical density of each sample at 340 nanoMeter was determined. The microtiter plate was then incubated at 37° C. for two hours. The optical density was again determined on the plate reader. This two-hour reading of optical density was then subtracted from the initial reading of optical density and termed the "delta OD 340."

For quality control purposes the positive control should have a delta OD 340 less than the delta OD 340 of the cutoff calibrator. The negative control should have a delta OD 340 which is greater than the delta OD 340 of the cutoff calibrator.

Results

Results for this example are given in Table 2.

TABLE 2

| Sample | Initial OD 340 | 2 HR OD 340 | Delta OD 340 |
|---|---|---|---|
| ACE Serum | 1151 | 852 | 299 |
| Negative Control | 1141 | 855 | 286 |
| Cut-off Calibrator | 1148 | 976 | 172 |
| Positive Control | 1172 | 1145 | 27 |
| Unknown 1 | 1388 | 1089 | 299 |
| Unknown 2 | 1553 | 1257 | 296 |
| Unknown 3 | 1291 | 975 | 316 |
| Unknown 4 | 1554 | 1512 | 42 |
| Unknown 5 | 1322 | 1026 | 296 |

To interpret these results, the ACE inhibitor activity is inversely proportional to the delta OD 340. Therefore, a sample containing unknown amounts of ACE-inhibiting drugs is positive for ACE inhibitors if the delta OD 340 of the sample is less than the cutoff calibrator delta OD 340. Conversely, a sample containing unknown amounts of ACE-inhibiting drugs is negative for ACE inhibitors if the delta OD 340 of the sample is greater than the cutoff calibrator delta OD 340. As shown in Table 2, unknown sample number 4 has a delta OD 340 (42) which is less than the delta OD 340 of the cutoff calibrator (172). This indicates that unknown sample number 4 is positive for ACE inhibiting drugs and, therefore, ACE inhibition activity.

EXAMPLE 2

This example demonstrated that the assay for ACE-inhibiting drugs identified many different medications from the family of ACE-inhibiting drugs.

Materials and Methods

Fluid samples were obtained from individuals reporting that they were currently taking an ACE-inhibiting drug. The samples and controls were assayed as in Example 1. The medications reported by the patients included eight different medications of the ACE-inhibiting drug family. Each individual reported taking only one specific ACE-inhibiting drug. Thus, this example tests the ability of the assay to identify individuals on ACE-inhibiting drugs without prior knowledge of the specific drug being taken.

Results

Results from this example are given below in Table 3.

TABLE 3

| DRUG | LISTED | DETECTED |
|---|---|---|
| BENAZEPRIL | 14 | 14 |
| CAPTOPRIL | 2 | 2 |
| ENALAPRIL | 5 | 5 |
| FOSINOPRIL | 6 | 5 |
| LISINOPRIL | 25 | 22 |
| MOEXIPRIL | 4 | 3 |
| RAMIPRIL | 2 | 2 |

TABLE 3-continued

| DRUG | LISTED | DETECTED |
|---|---|---|
| QUINAPRIL | 15 | 15 |
| TOTAL | 73 | 68 |

In this example, 93.1% of urine samples from individuals self-reporting ACE use tested positive for ACE-inhibiting drugs. Thus, the enzyme specific assay for the detection of therapeutic drugs works and one enzyme assay can detect all members of a drug class or family. Additionally, the assay is superior to antibody based amino assays in that no antibody needs to be produced for each drug to be tested for. In other words, the enzyme-based assay can detect all members of a drug class while an antibody-based immunoassay potentially detects only the specific drug that the antibody was developed against. Of course, the 93.1% identification rate assumes that all patients that reported taking the medications had actually taken their prescribed medications as instructed.

EXAMPLE 3

This example provides a cell receptor assay for B1 adrenergic receptors and tests the accuracy of the assay. Patient urine that may or may not contain target ligand and a radiolabeled competitive ligand are added to a test tube containing a limited concentration of cell membrane containing beta-1-adrenergic receptors. The unlabeled ligand in the patient's urine competes with the labeled ligand for the receptor sites during an incubation period. Following incubation the tubes are centrifuged to precipitate the cell membrane-receptors. The solution containing unbound ligand is decanted and the radioactivity retained in the tubes is detected in a gamma counter. The amount of radioactivity bound is indirectly proportional to the concentration of unlabeled ligand present in the patient's urine.

Materials and Methods

Tris working buffer (Sigma Chemical) Dissolve 4.55 grams of Tris base, 1.27 g MgCl2 (hexahydrate), 0.37 g disodium dihydrate ethylenediaminetetraacetic acid, and 0.5 g ascorbic acid in 450 milliliter of deionized water. Adjust the pH to 7.4 with concentrated hydrochloric acid and fill to volume with deionized water.

Beta-1-adrenergic receptor containing membranes (Sigma Chemical #RBIB-143). Thaw the stock solution of membrane and dilute to 30 milliliter with Tris working buffer.

Radiolabeled 125-iodocyanopindolol (100 microCurries #IM142 Amersham Pharmacia Biotech Piscataway, N.J.) a stock solution of iodocyanopindolol is prepared by diluting 100 uCi of Amersham Pharmacia provided stock with 4.9 milliliter of Tris working buffer. The working solution of radiolabel is prepared by diluting the stock 1 to 30 with Tris working buffer. Drug free urine is obtained from UTAK Laboratories, Valencia, Calif. Atenolol, Propranolol, Metoprolol were from Sigma Chemical Company St. Louis, Mo. Atenolol, propranolol and metoprolol were diluted with HPLC grade ethyl alcohol (Aldrich Chemical Company Milwaukee, Wis.) to produce a 1.0 mg/ml stock solution for each drug. A cut-off control was prepared by dilution of 100 ul of stock solution of tenolol with 4.9 milliliter of UTAK drug negative urine, nominal concentration 20 ug/ml.

Samples, controls and the cut-off calibrator are diluted 1 to 10 with working buffer prior to assay. 100 microliter of Tris working buffer, 25 ul of diluted sample, cut-off calibrator, or control, 25 ul of diluted radiolabeled iodocyanopindolol, and 50 ul of working membrane solution were added to a 12×75 millimeter test tube. The solution was mixed by vortex and incubated for two hours at room temperature. After incubation, 1 ml of ice cold Tris working buffer was added to each tube and then centrifuged at 4,000 rpms in a Clay Adams CA6000, (Becton Dickinson Microbiological Systems Sparks, Md.) for 10 minutes. The supemate was decanted off and the tops of the tubes were blotted. The total radioactivity was detected on Packard Cobra II Auto Gamma counter (Packard Instrument Company Downers Grove, Ill.). The cut-off was calculated by multiplying the value for 20 ug/ml of Atenolol times 1.4. The calculated value is 1.4×5117=7164

TABLE 2

Beta-1-adrenergic-blocker study

| Sample Number | Counts per Minute | Interpretation | HPLC (Yes/No) |
|---|---|---|---|
| 1 | 720 | Positive | |
| 2 | 5783 | Positive | |
| 3 | 2932 | Positive | |
| 4 | 2769 | Positive | |
| 5 | 5192 | Positive | |
| 6 | 6588 | Positive | |
| 7 | 1393 | Positive | |
| 8 | 3244 | Positive | |
| 9 | 5117 | Cut-off atenolol | |
| 10 | 6026 | Positive | |
| 11 | 1156 | Positive | |
| 12 | 11509 | Negative | |
| 13 | 9659 | Negative | |
| 14 | 13884 | Negative | |
| 15 | 7432 | Negative | |
| 16 | 12561 | Negative | |
| 17 | 13178 | Negative | |
| 18 | 10502 | Negative | |
| 19 | 6959 | Positive | |
| 20 | 9865 | Negative | |
| 21 | 7665 | Negative | |
| 22 | 8706 | Negative | |
| 23 | 8708 | Negative | |
| 24 | 12421 | Negative | |

All positive samples were identified correctly, while one negative (1/13) also tested positive. The over-all correlation was calculated to be 95.8%.

We claim:

1. A method of determining the presence of an active angiotensin converting enzyme (ACE)-inhibiting drug present in a fluid sample, said ACE-inhibiting drug in its active state modifying the activity level of ACE on a substrate, wherein said substrate is specific for ACE, said method comprising the steps of:

providing a first fluid sample obtained from a patient that may contain any of said ACE-inhibiting drug, said first fluid sample being a serum or urine sample and including ACE;

adding a quantity of said substrate to said first fluid sample;

measuring the activity level of ACE on said substrate;

comparing said measured activity level with a standard activity level established by testing serum or urine samples from a plurality of individuals other than the patient that have a known quantity of active ACE-inhibiting drug present; and determining the presence of said active ACE-inhibiting drug by the measured activity level compared to said standard activity level.

2. The method of claim 1, said standard activity level representing the activity level of said enzyme on a known quantity of said substrate.

3. The method of claim 1 further comprising the step of correlating said measured activity level with the concentration of said active ACE-inhibiting drug.

4. The method of claim 1, said standard activity level representing the activity level of said ACE on a known quantity of said substrate.

5. The method of claim 1, said ACE activity level decreasing when said active ACE-inhibiting drug is present.

6. The method of claim 1, said ACE activity level increasing as the level of active ACE-inhibiting drug in said sample decreases.

7. The method of claim 1, said ACE activity level decreasing as the level of said active ACE-inhibiting drug in said sample increases.

8. The method of claim 1, wherein said ACE-inhibiting drugs is selected from the group consisting of benazepril, captopril, enalapril, fosinopril, lisinopril, quinapril, ramipril, and trandolapril and combinations thereof.

9. The method of claim 1, wherein said determining step comprises the step of measuring the optical density of said fluid sample.

10. The method of claim 1, wherein said activity level is correlated with the optical density at 340 nm ($O.D._{340}$) and is inverse of the delta $O.D._{340}$ number.

* * * * *